(12) United States Patent
Boettner et al.

(10) Patent No.: US 11,925,420 B2
(45) Date of Patent: Mar. 12, 2024

(54) ADJUSTMENT SYSTEM AND METHOD FOR PATIENT POSITION INTRAOPERATIVELY USING RADIOGRAPHIC MEASUREMENTS

(71) Applicant: AccuJoint, Inc, Larchmont, NY (US)

(72) Inventors: Friedrich Boettner, Larchmont, NY (US); Ajay Premkumar, Decatur, GA (US)

(73) Assignee: ACCUPREDICT, INC., Larchmont, NY (US)

( * ) Notice: Subject to any disclaimer, the term of this patent is extended or adjusted under 35 U.S.C. 154(b) by 0 days.

(21) Appl. No.: 17/839,203

(22) Filed: Jun. 13, 2022

(65) Prior Publication Data

US 2022/0323159 A1    Oct. 13, 2022

Related U.S. Application Data

(63) Continuation-in-part of application No. 17/666,174, filed on Feb. 7, 2022, now abandoned, which is a
(Continued)

(51) Int. Cl.
*A61B 34/10*  (2016.01)
*A61B 6/00*   (2006.01)
(Continued)

(52) U.S. Cl.
CPC ............ *A61B 34/20* (2016.02); *A61B 6/12* (2013.01); *A61B 6/487* (2013.01);
(Continued)

(58) Field of Classification Search
CPC ...... A61B 34/10; A61B 34/101; A61B 34/107
See application file for complete search history.

(56) References Cited

U.S. PATENT DOCUMENTS 6,567,681 B1    5/2003  Lindequist
2005/0251113 A1  11/2005  Kienzle, III
(Continued)

OTHER PUBLICATIONS

Yutaka Inaba et al., "Preoperative planning for implant placement with consideration of pelvic tilt in total hip arthroplasty: postoperative efficacy evaluation", BMC Musculoskeletal Disorders, Dec. 2016.
(Continued)

*Primary Examiner* — Nicholas W Woodall
(74) *Attorney, Agent, or Firm* — Leason Ellis LLP

(57) ABSTRACT

A system and method provide for image-guided implant placement as a function of at least one intraoperative image during a surgical procedure. At least one computing device is configured by executing code stored in non-transitory processor readable media to process at least one preoperative image to assess axial rotation and/or sagittal pelvic inclination. Further, as a function of a plurality of identified anatomical landmarks in the at least one preoperative image, at least one of distances, angles, and areas is measured. Thereafter, as a function of calculations associated with the at least one of distances, angles, and areas, axial rotation associated with at least one image is measured. Thereafter, at least one value associated with placement of an implant during the surgical procedure is adjusted and information associated therewith is provided via a graphical user interface.

23 Claims, 12 Drawing Sheets

Related U.S. Application Data continuation of application No. 16/163,504, filed on Oct. 17, 2018, now Pat. No. 11,241,287, which is a continuation-in-part of application No. 15/501,671, filed as application No. PCT/US2016/045710 on Aug. 5, 2016, now Pat. No. 10,238,454.

(60) Provisional application No. 63/209,656, filed on Jun. 11, 2021, provisional application No. 63/279,481, filed on Nov. 15, 2021, provisional application No. 62/573,288, filed on Oct. 17, 2017, provisional application No. 62/201,417, filed on Aug. 5, 2015.

(51) Int. Cl.

| | | |
|---|---|---|
| *A61B 6/12* | (2006.01) | |
| *A61B 17/17* | (2006.01) | |
| *A61B 34/00* | (2016.01) | |
| *A61B 34/20* | (2016.01) | |
| *A61F 2/32* | (2006.01) | |
| *A61F 2/46* | (2006.01) | |
| *A61B 17/00* | (2006.01) | |
| *A61B 17/15* | (2006.01) | |
| *A61B 17/16* | (2006.01) | |
| *A61B 90/00* | (2016.01) | |

(52) U.S. Cl.
CPC ...... *A61B 17/1703* (2013.01); *A61B 17/1746* (2013.01); *A61B 34/10* (2016.02); *A61B 34/25* (2016.02); *A61F 2/32* (2013.01); *A61F 2/4609* (2013.01); *A61F 2/4657* (2013.01); *A61B 6/4441* (2013.01); *A61B 2017/0092* (2013.01); *A61B 17/15* (2013.01); *A61B 17/1666* (2013.01); *A61B 2034/104* (2016.02); *A61B 2034/107* (2016.02); *A61B 2034/108* (2016.02); *A61B 2034/2068* (2016.02); *A61B 2034/254* (2016.02); *A61B 2090/376* (2016.02)

(56) References Cited

U.S. PATENT DOCUMENTS

| | | | |
|---|---|---|---|
| 2006/0264731 A1* | 11/2006 | Murphy | ............ A61F 2/4657 600/407 |
| 2011/0249875 A1 | 10/2011 | Dewaele | |
| 2015/0119966 A1 | 4/2015 | Richter et al. | |
| 2020/0022758 A1* | 1/2020 | Shoham | ............ A61B 5/0077 |
| 2020/0323649 A1 | 10/2020 | Schipper et al. | |
| 2020/0352529 A1 | 11/2020 | Wollowick et al. | |
| 2022/0249248 A1* | 8/2022 | Schipper | ............ A61B 34/25 |

OTHER PUBLICATIONS

International Search Report and Written Opinion for corresponding PCT Application No. PCT/US2022/033270 dated Oct. 5, 2022 (12 pages).

\* cited by examiner

ADJUSTMENT SYSTEM AND METHOD FOR PATIENT POSITION INTRAOPERATIVELY USING RADIOGRAPHIC MEASUREMENTS

CROSS REFERENCE TO RELATED APPLICATIONS

This patent application is based on and claims priority to U.S. Provisional Patent Application Ser. No. 63/209,656, filed Jun. 11, 2021 and to U.S. Provisional Patent Application Ser. No. 63/279,481 filed Nov. 15, 2021, and further this patent application is a continuation-in-part of U.S. Non-Provisional patent application Ser. No. 17/666,174, filed Feb. 7, 2022, which is a continuation of U.S. Non-Provisional patent application Ser. No. 16/163,504, filed Oct. 17, 2018 now issued as U.S. Pat. No. 11,241,287 on Feb. 8, 2022, which is based on and claims priority to U.S. Provisional Patent Application Ser. No. 62/573,288, filed Oct. 17, 2017, and which is a continuation-in-part of U.S. Non Provisional patent application Ser. No. 15/501,671, filed Feb. 3, 2017 now issued as U.S. Patent Ser. No. 10,238,454 on Mar. 26, 2019, which is a U.S. National Phase Application under 35 U.S.C. § 371 of International Patent Application No. PCT/US16/45710, filed Aug. 5, 2016, which claims priority to U.S. Provisional Patent Application Ser. No. 62/201,417, filed Aug. 5, 2015, all of which are incorporated by reference, as if expressly set forth in their respective entireties herein.

FIELD

The present disclosure relates, generally, to the field of surgery and, more particularly, to a specific application in image-guided total hip replacement.

BACKGROUND

Surgeries are commonly performed utilizing radiographs, including intraoperative radiographs. Unfortunately, radiographs can be affected by patient positioning at the time of image capture, and measurements obtained using the radiographs, particularly changes over time, can be misleading. This is especially true in the field of total joint replacement, where precise implant positioning including the acetabular and femoral component is paramount for a successful outcome.

It is with respect to these and other considerations that the disclosure made herein is presented.

BRIEF SUMMARY

A system and method provide for image-guided implant placement. In one or more implementations of the present disclosure, at least one computing device is configured by executing code stored in non-transitory processor readable media to determine a value representing absolute axial rotation by processing at least one pelvic image presenting a lateral view and at least one pelvic image presenting an AP view. For example, the at least one lateral image is a preoperative image and the at least one AP image is an intraoperative image. Using a plurality of identified anatomical landmarks in at least one of the images, measurements can be made for at least one of distances, angles, and areas. Thereafter, as a function of calculations associated with at least one of the distances, angles, and areas, the value representing absolute axial rotation of the pelvis can be determined. The pelvic images can be provided via radiography, fluoroscopy, or both.

In one or more implementations of the present disclosure, at least one computing device is configured by executing code stored in non-transitory processor readable media to determine a value representing a change in axial rotation by processing at least one pelvic image presenting a lateral view and at least two pelvic images presenting an AP view. For example, at least one of the AP images is a preoperative image and at least one of the AP images is an intraoperative image. Using a plurality of identified anatomical landmarks in at least one of the images, measurements can be made for at least one of distances, angles, and areas. Thereafter, as a function of calculations associated with at least one of the distances, angles, and areas, the value representing a change in axial rotation can be determined.

In one or more implementations of the present disclosure, at least one computing device is configured by executing code stored in non-transitory processor readable media to determine a value representing change in sagittal pelvic inclination by processing at least one pelvic image presenting a lateral view and at least two pelvic images presenting an AP view. For example, the at least one lateral image is a preoperative image and at least two pelvic images presenting an AP view. Using a plurality of identified anatomical landmarks in at least one of the images, measurements can be made of at least one of distances, angles, and areas. Thereafter, as a function of calculations associated with at least one of the distances, angles, and areas, the value representing change in pelvic sagittal inclination between the respective AP images can be determined. For example, the value can represent an amount of degrees of change in pelvic sagittal inclination from a preoperative to an intraoperative AP image.

In one or more implementations of the present disclosure, at least one computing device is configured by executing code stored in non-transitory processor readable media to use machine learning and artificial intelligence to determine a value representing predicted absolute axial rotation by processing at least one AP image and/or a value representing predicted change in pelvic sagittal inclination by processing at least two AP images. For example, a plurality of training images (including lateral images and respective AP images) are processed for training to determine the absolute axial rotation and pelvic sagittal inclination as described above. Anatomical landmarks in the training images can then be identified and used for measuring at least one of distances, angles, and areas. Thereafter, as a function of calculations associated with at least one of the distances, angles, and areas in the training images, values representing absolute axial rotation and change in pelvic sagittal inclination can be determined. Once trained, a value representing absolute axial rotation can be predicted using a single pelvic AP image, as a function of artificial intelligence and machine learning, including based on at least one of distances, angles, and areas measured in the single pelvic AP image. In addition, a value representing change in sagittal pelvic inclination can be predicted using two pelvic AP images, as a function of artificial intelligence and machine learning, including based on at least one of distances, angles, and areas measured in the two pelvic AP images.

Other features of the present disclosure are shown and described herein.

BRIEF DESCRIPTION OF THE DRAWINGS

Aspects of the present disclosure can be more readily appreciated upon review of the detailed description of its various embodiments, described below, when taken in conjunction with the accompanying drawings, of which.

DETAILED DESCRIPTION OF THE EMBODIMENTS

Figure 1:
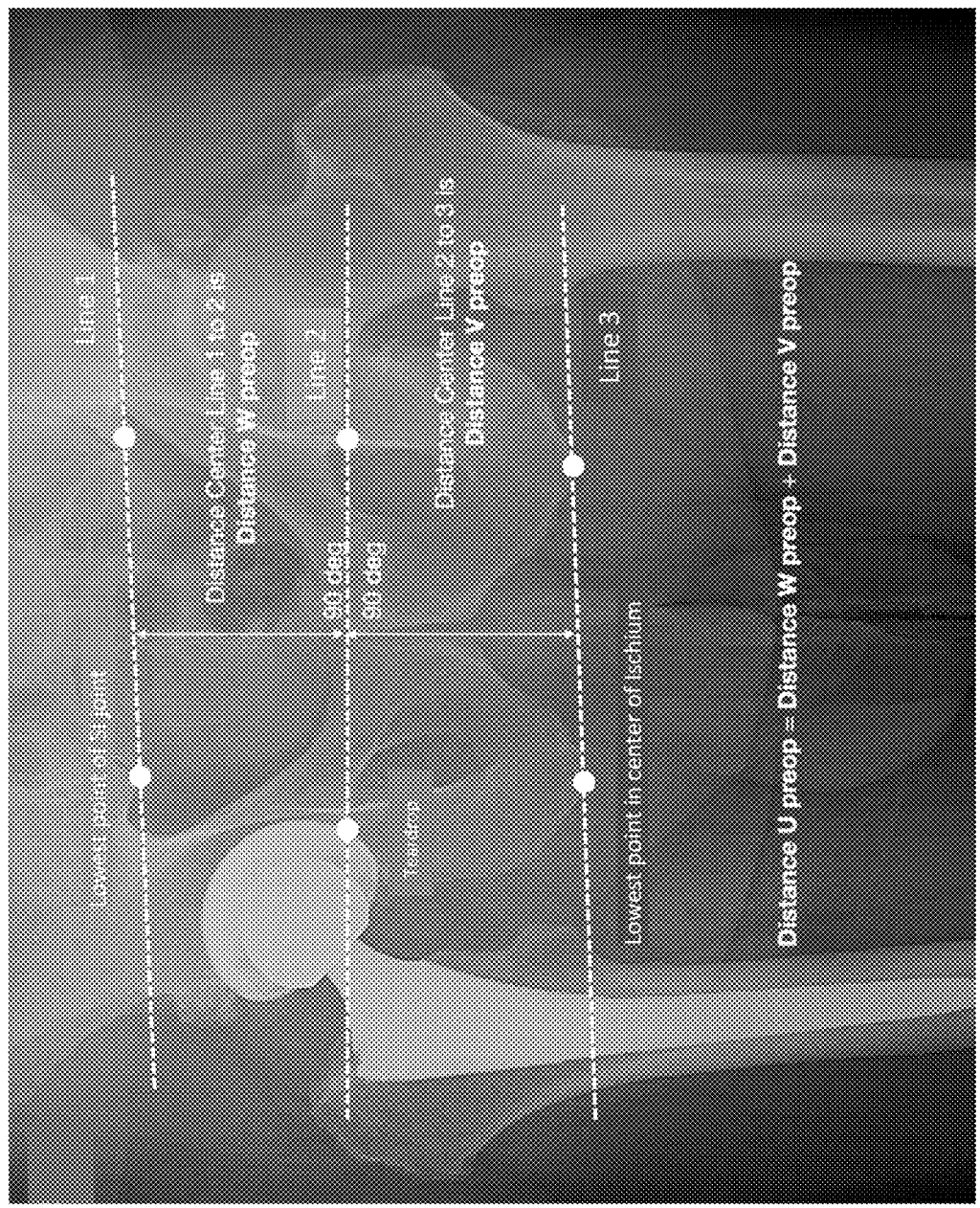
FIG. 1 illustrates an AP pelvis radiograph with three lines (Line 1, Line 2, and Line 3) drawn thereon.

By way of summary and introduction, the present disclosure includes a plurality of technological features, vis-à-vis user computing devices that include specially configured hardware for image guidance in connection with surgical implant positioning. The combination of features set forth in the present disclosure include, for example, providing a system and method to determine and adjust implant positioning after determining changes in intraoperative patient position, as opposed to patient position in preoperative or expected postoperative images. Furthermore, one or more computing devices can be configured to detect changes in three-dimensional space, as a function of the teachings herein. In one or more implementations, analyses are made of radiographs or other images that represent, for example, preoperative, intraoperative, and/or expected postoperative images of the pelvis. Using automatically identified anatomical landmarks shown in one or more radiographs, respective distances, angles, and areas can be generated and used to determine changes in patient positioning and to calculate more accurate implant positioning. For example, adjustments can be made, using measurements based on locations of identified anatomical landmarks, to implant placement, thereby increasing accuracy.

In one or more implementations, a system and method are provided that include at least one computing device that can interface with one or more devices for acetabular cup position adjustment, such as until the cup is in line (in registration) with the data. In addition, one or more computing devices can provide, for example, a graphical user interface that can be configured to display one or more images (e.g., radiographs), as well as tools for a user to be alerted, for example, when implant position is achieved. One or more navigational instruments can be in communication with hardware, including as shown and described in commonly owned U.S. Pat. No. 11,241,287, which is incorporated by reference herein, and can be configured to adjust the position of the acetabular cup. One or more navigational instruments can include or provide navigational markers which are usable to calculate the location of the navigated instrument and, correspondingly, a cup that can be coupled thereto. An acetabular cup's movements, therefore, can be detected and measured substantially in real-time. The control console or other hardware described herein can thus provide instructions (which can be displayed on the display) to the user directing how the acetabular cup should be positioned and/or repositioned with the patient.

It is recognized that various forms of computing devices can be used and provided in accordance with the present disclosure, including server computers, personal computers, tablet computers, laptop computers, mobile computing devices (e.g., smartphones), or other suitable device that is configured to access one or more data communication networks and can communicate over the network to the various machines that are configured to send and receive content, data, as well as instructions. Content and data provided via one or more computing devices can include information in a variety of forms, including, as non-limiting examples, text, audio, images, and video, and can include embedded information such as links to other resources on the network, metadata, and/or machine executable instructions. Each computing device can be of conventional construction, and may be configured to provide different content and services to other devices, such as mobile computing devices, one or more of the server computing devices. Devices can comprise the same machine or can be spread across several machines in large scale implementations, as understood by persons having ordinary skill in the art. In relevant part, each computer server has one or more processors, a computer-readable memory that stores code that configures the processor to perform at least one function, and a communication port for connecting to the network. The code can comprise one or more programs, libraries, functions or routines which, for purposes of this specification, can be described in terms of a plurality of modules, residing in a representative code/instructions storage, that implement different parts of the process described herein.

Further, computer programs (also referred to herein, generally, as computer control logic or computer readable program code), such as imaging software, can be stored in a main and/or secondary memory and implemented by one or more processors (controllers, or the like) to cause the one or more processors to perform the functions of the invention as described herein. In this document, the terms "memory," "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like. It should be understood that, for mobile computing devices (e.g., tablet), computer programs such as imaging software can be in the form of an app executed on the mobile computing device Referring to the drawings, in which like reference numerals refer to like elements, FIG. 1 illustrates an example graphical user interface provided in accordance with one or more implementations of the present disclosure. As shown in FIG. 1, an antero-posterior ("AP") radiograph of a pelvis is shown, with three lines (Line 1, Line 2, and Line 3) drawn thereon. In the example shown in FIG. 1, Line 1 has been drawn between the inferior aspect of the sacroiliac joints. Line 2 is drawn between the inferior aspect of the acetabular teardrops. Line 3 is drawn between the two most inferior aspects of the ischium, and can be adjusted for significant bony abnormalities, such as the presence of excessive bone spurs. The distances between the midpoint of these lines are recorded on each AP pelvis image and used to contribute to measuring change in pelvic sagittal tilt between images, such as two AP pelvic radiographs.

The following notations are represented in the drawings.

Distance W Preop represents the distance between the point on Line 2 which corresponds to the center of the pubic symphysis and a point directed superiorly at a 90-degree angle from this line to intersect Line 1 on the preoperative image AP Pelvis Image.

Distance V Preop represents the distance between the point on Line 2 which corresponds to the center of the pubic symphysis and a point directed inferiorly at a 90-degree angle from this line to intersect Line 3 on the preoperative AP Pelvis Image.

Distance U Preop represents the sum of Distance W Preop and Distance V Preop.

Similar measurements can be made intraoperatively or postoperatively.

As an example, for an intraoperative measurement:

Distance W Intraop represents the distance between the point on Line 2 which corresponds to the center of the pubic symphysis and a point directed superiorly at a 90-degree angle from this line to intersect Line 1 on the intraoperative image AP Pelvis Image.

Distance V Intraop represents the distance between the point on Line 2 which corresponds to the center of the pubic symphysis and a point directed inferiorly at a 90-degree angle from this line to intersect Line 3 on an intraoperative AP Pelvis Image.

Figure 2A:
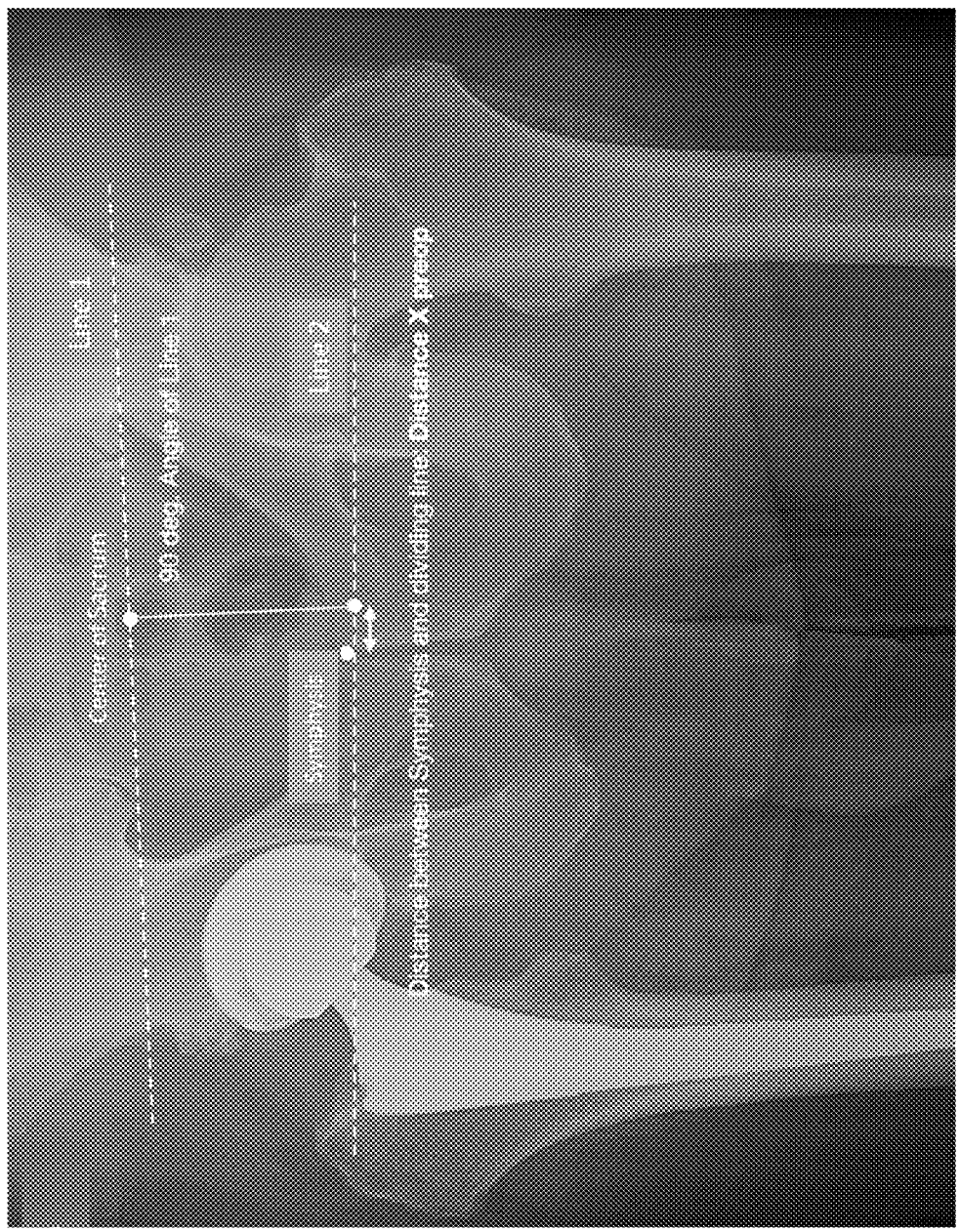
FIGS. 2A-2B illustrate steps in a methodology to assess pelvic axial rotation, in accordance with an implementation of the present disclosure.
Figure 2B:
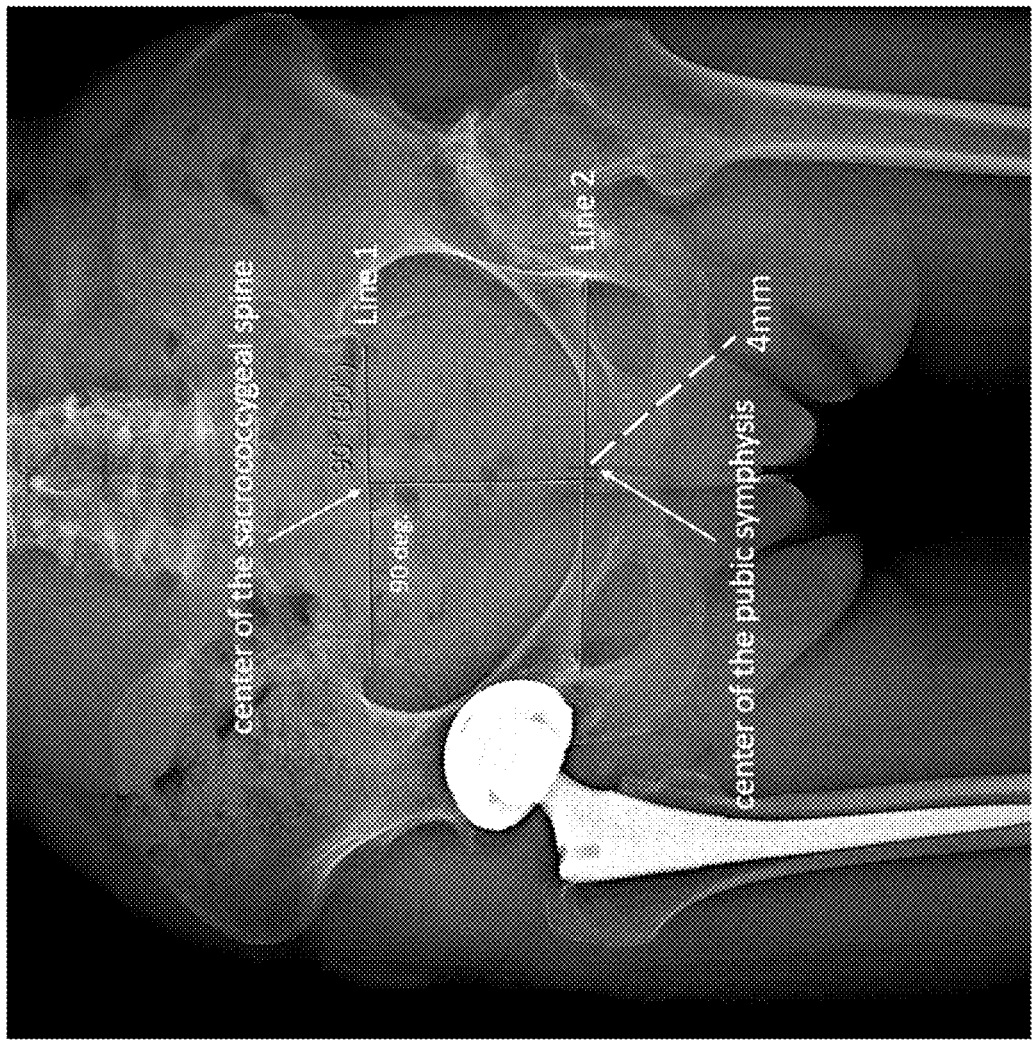

Distance U Intraop represents the sum of Distance W Intraop and Distance V Intraop FIGS. 2A-2B illustrate steps in a methodology to assess pelvic axial rotation, in accordance with an implementation of the present disclosure. In FIG. 2A, for example, an AP pelvis radiograph is obtained, and Line 1 and Line 2 are drawn, as shown and described with reference in FIG. 1. Next, as illustrated in FIG. 2A, a line extending from Line 1 to Line 2 is drawn. The apex on Line 1 corresponds to the intersection of Line 1 and the center of the sacrococcygeal spine. This line is extended inferiorly in a perpendicular fashion to Line 2. The distance between the intersection of this line and the center of the pubic symphysis on Line 2 is then measured (Distance X Preop on a preoperative image, Distance X Intraop on an intraoperative image, or the like). This measurement can contribute to measuring pelvic axial rotation as well as change in pelvic axial rotation between images. FIG. 2B illustrates another AP pelvis radiograph and shows Line 1 and Line 2 in accordance with one or more implementations of the present disclosure.

Figure 3A:
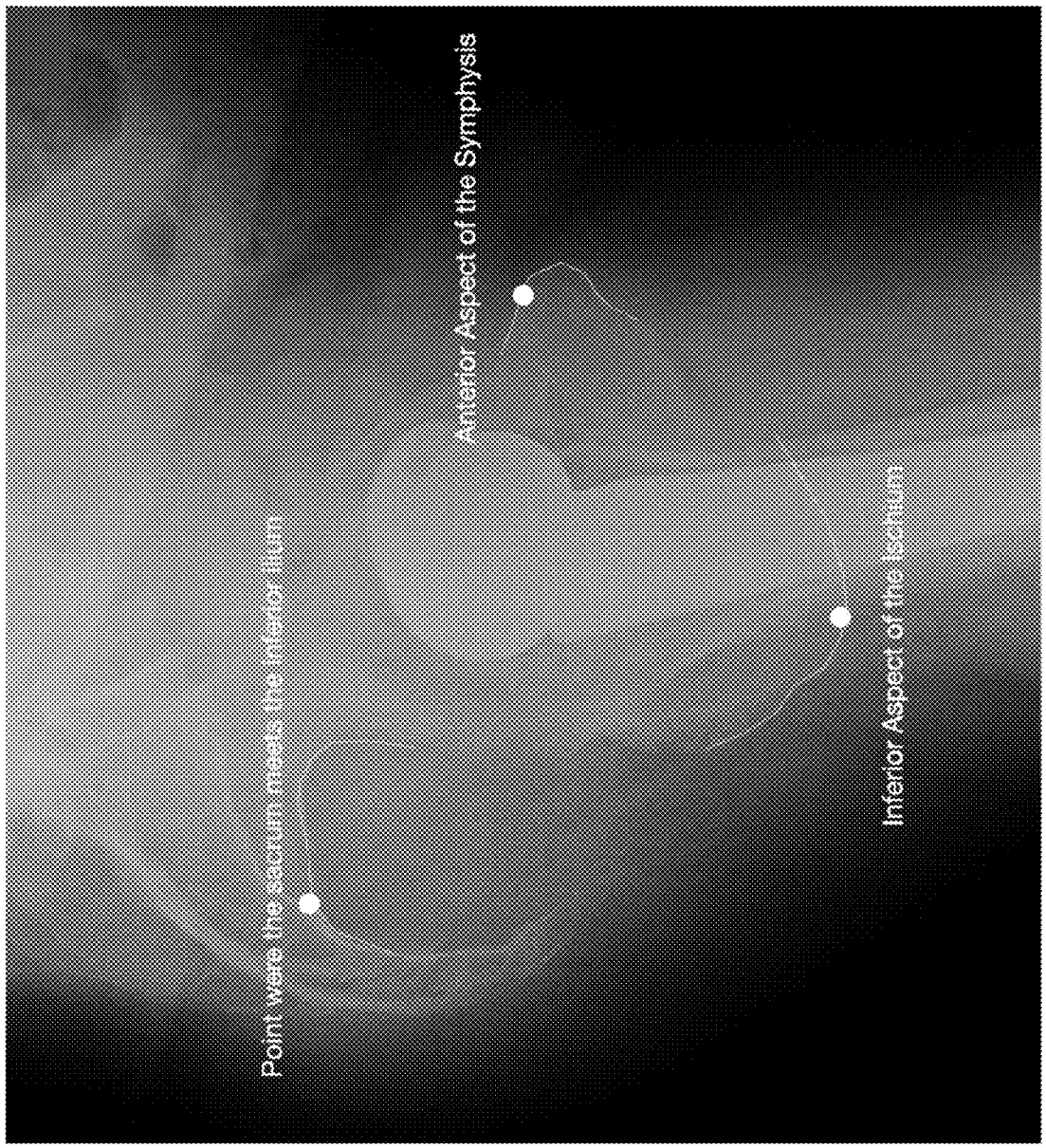
FIGS. 3A-3C illustrate example lateral pelvic radiographs.
Figure 3B:
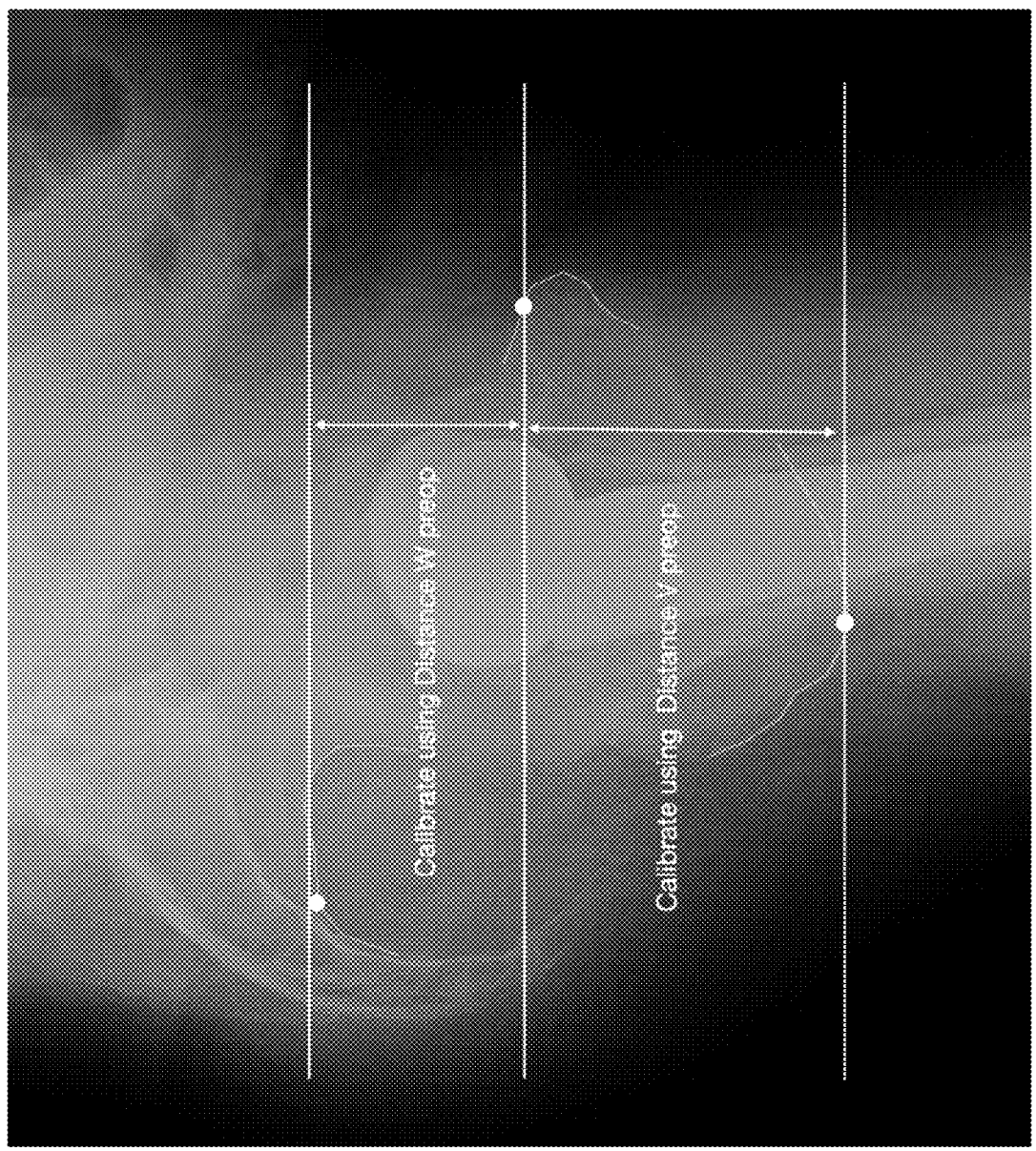
Figure 3C:
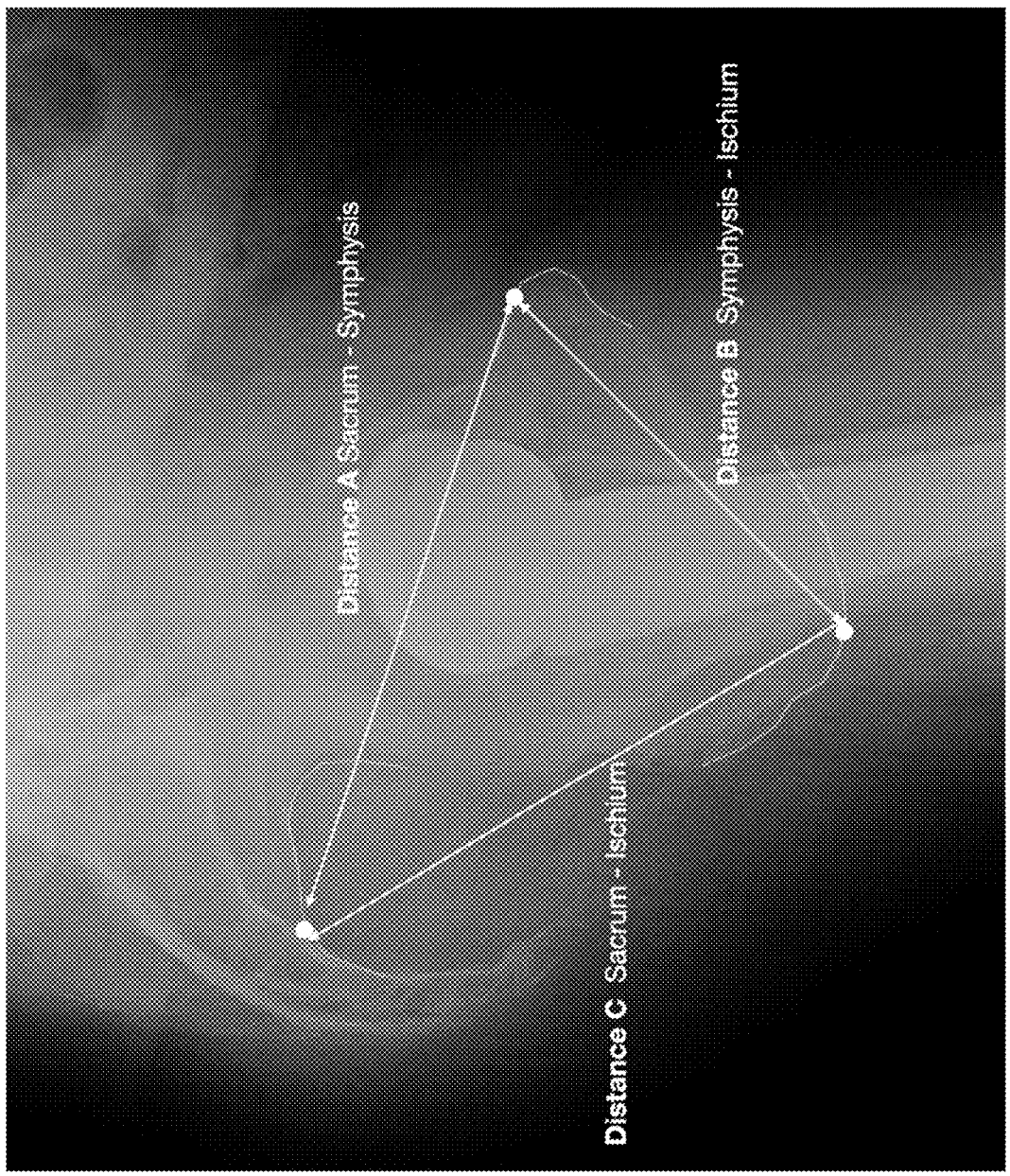

FIGS. 3A, 3B and 3C illustrate example lateral pelvic radiographs. FIG. 3A illustrates three points on the radiograph: the anterior aspect of the pubic symphysis, the inferior aspect of the ischium, and the point where the sacrum meets the posterior ilium. FIG. 3B illustrates how the image is calibrated using measurements from the calibrated AP Pelvis Image (FIG. 1). FIG. 3C illustrates the distances (Distance A, B, C) between these points are measured and used as a component of a measurement for pelvic axial rotation as well as change in pelvic sagittal tilt between radiographs.

To calculate the axial rotation of the preoperative image, Z is calculated as the $$Z = \sqrt{Distance A^2 - Distance W Preop^2}$$

Axial rotation is calculated as:

$$\text{axial rotation} = \tan^{-1}\left(\frac{Distance \times Preop}{Z}\right) * 57.2958.$$

Similarly, axial rotation on any successive (intraoperative or postoperative) image AP Pelvis radiograph or C-arm (Fluoroscopy) image can be calculated:

$$\text{axial rotation intraop} = \tan^{-1}\left(\frac{Distance \times Intraop}{Z}\right) * 57.2958.$$

In addition, changes in pelvic sagittal tilt on an intraoperative or postoperative image in relationship to the pelvic tilt on the preoperative image can be calculated in the following fashion. This change is calculated based on the measurements on the preoperative lateral pelvis image (FIG. 3A).

If all three distances (Distance A, Distance B and Distance C) are measured, the change can be calculated in the following fashion:

Change in Pelvic Sagittal Tilt based on Distance A (FIG. 3A):

$$\text{Preoperative Tilt in degree} = P^A = \sin^{-1}\left(\frac{Distance\ W\ Preop}{Distance\ A}\right) * 57.2958$$

$$\text{Intraoperative Tilt in degree} = I^A = \sin^{-1}\left(\frac{Distance\ W\ Intraop}{Distance\ A}\right) * 57.2958$$

Change in Tilt based on Distance $A$ = Change $A = I^A - P^A$

Change in Pelvic Sagittal Tilt based on Distance B (FIG. 3B):

$$\text{Preoperative Tilt in degree} = P^B = \sin^{-1}\left(\frac{Distance\ V\ Preop}{Distance\ B}\right) * 57.2958$$

$$\text{Intraoperative Tilt in degree} = I^B = \sin^{-1}\left(\frac{Distance\ V\ Intraop}{Distance\ B}\right) * 57.2958$$

Change in Tilt based on Distance $A$ = Change $B = I^B - P^B$.

Change in Pelvic Sagittal Tilt based on Distance C (FIG. 3C):

$$\text{Preoperative Tilt in degree} = P^C = \sin^{-1}\left(\frac{Distance\ U\ Preop}{Distance\ C}\right) * 57.2958$$

$$\text{Intraoperative Tilt in degree} = I^C = \sin^{-1}\left(\frac{Distance\ U\ Intraop}{Distance\ C}\right) * 57.2958$$

Change in Tilt based on Distance $A$ = Change $C = I^C - P^C$.

The change of Pelvic sagittal tilt is calculated =

$$\frac{\text{Change } A + (-1 * \text{Change } B) + \text{Change } C}{3}.$$

If only one of the distances is available, then the change in Pelvic tilt in comparison to the tilt on the preoperative image is calculated as either Change A, Change B or Change C, rather than an average between them.

In accordance with the teachings herein, once the amount of axial rotation of the pelvis and sagittal tilt of the pelvis is known, the measurement of the acetabular component during total hip arthroplasty can be corrected, as can measurements for femoral offset and leg length when inserting the femoral component while using x-ray imaging (fluoroscopy). Axial rotation of the pelvis to the opposite site increases anteversion and decreases inclination of the acetabular component on radiographs. Moreover, increased forward sagittal tilt decreases acetabular component inclination and anteversion, while increased backward sagittal tilt (pelvic roll back) increases acetabular component inclination and anteversion. Changes in pelvic axial rotation also impact the measurement of leg length and offset for both hips. The changes can be calculated based on changes in pelvic sagittal tilt and axial rotation and used for measurement corrections.

Figure 4:
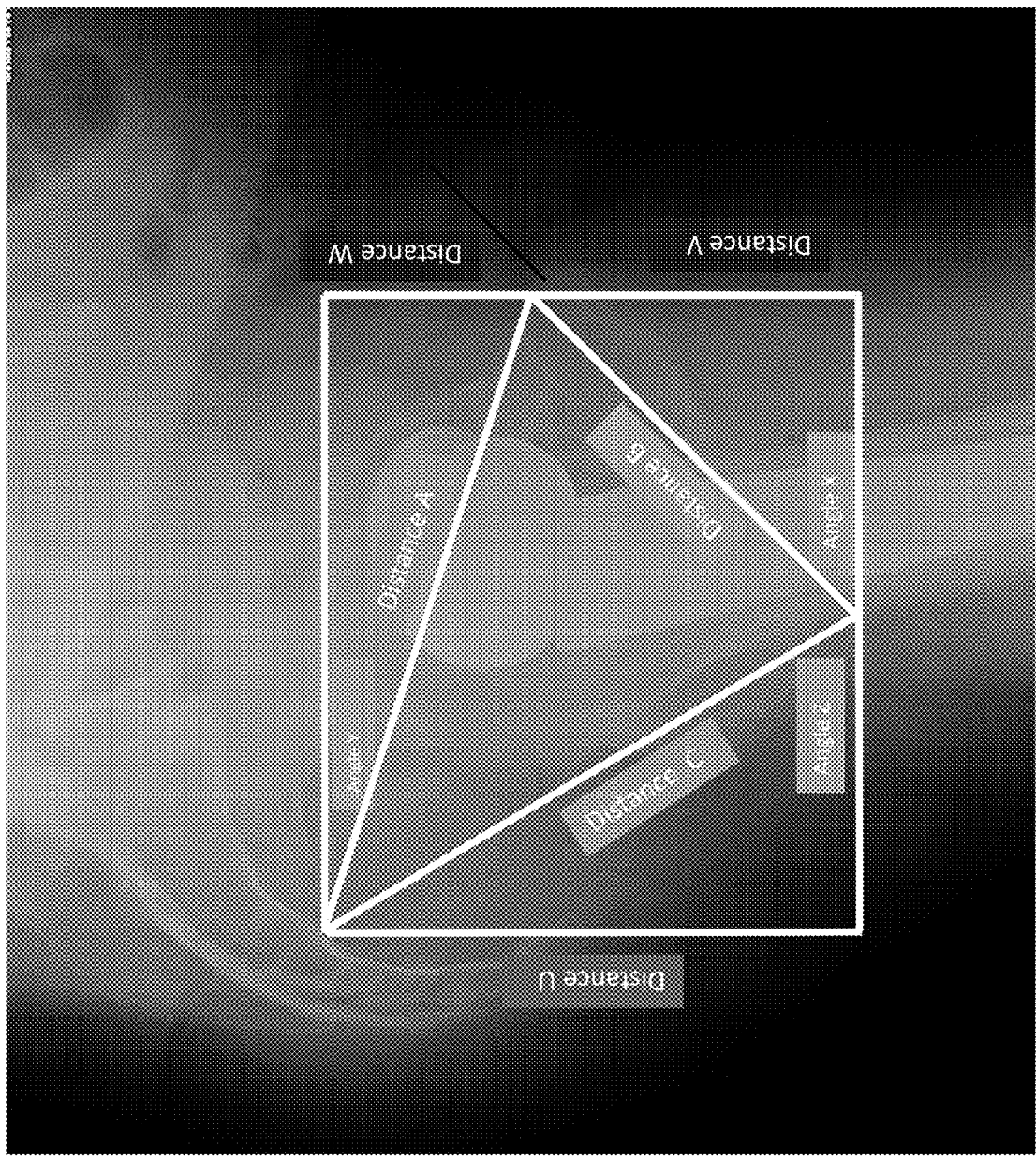
FIG. 4. is a diagrammatic representation of the three points on a lateral radiograph, as shown and described in FIG. 3.
Figure 5A:
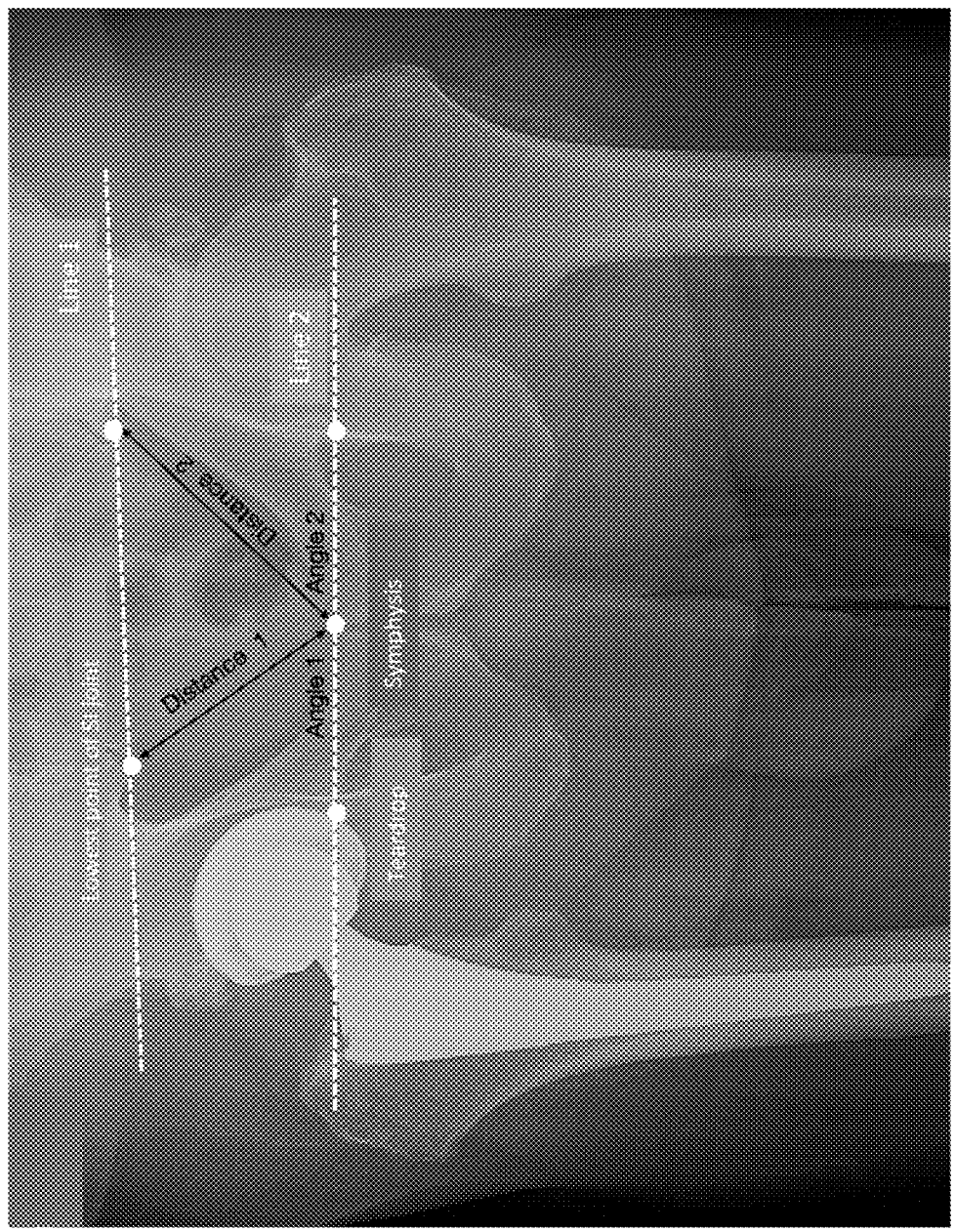
FIGS. 5A-5E illustrate example radiographs and other variables to correlate axial rotation and pelvic tilt.
Figure 5B:
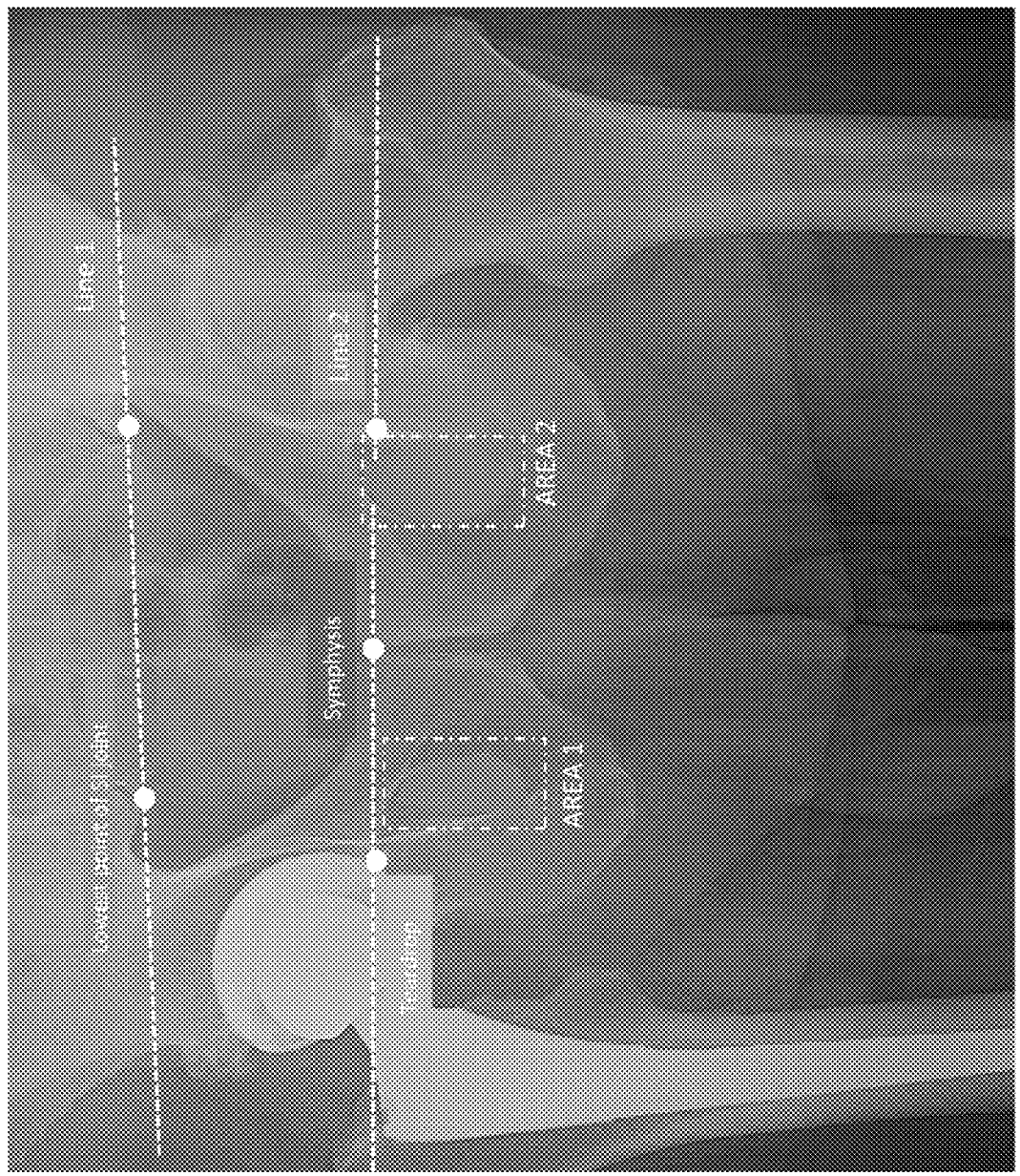
Figure 5C:
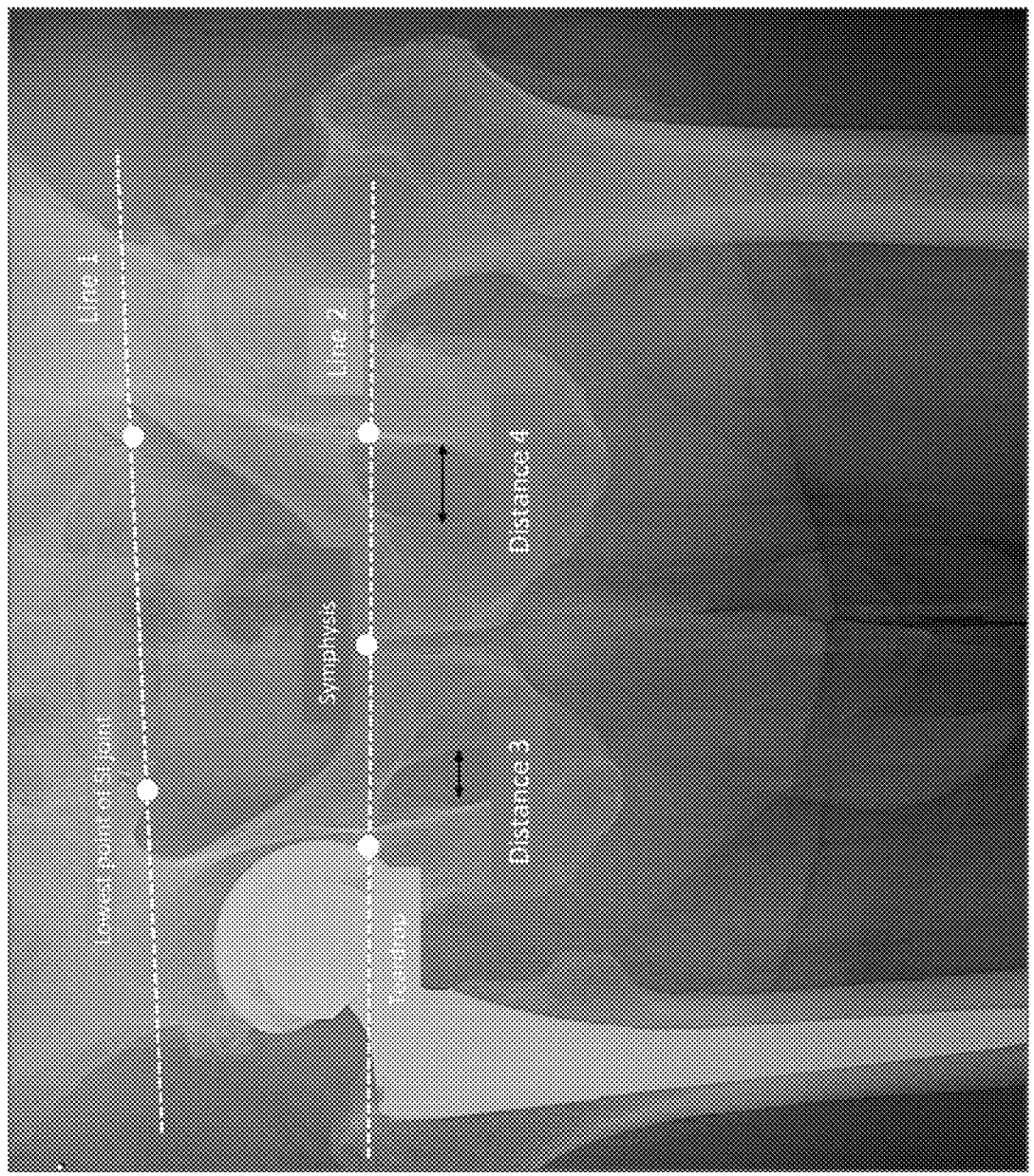
Figure 5D:
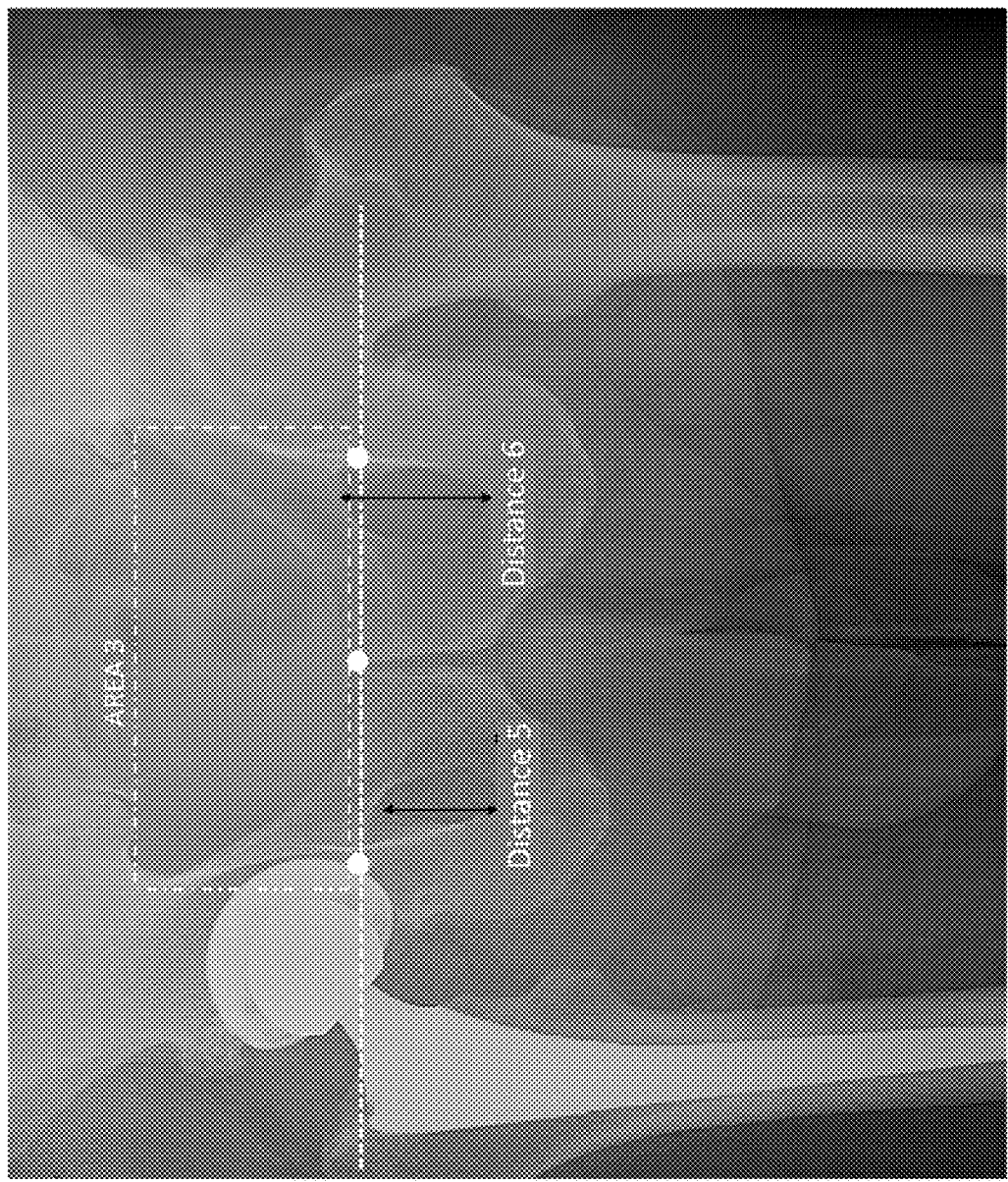
Figure 5E:
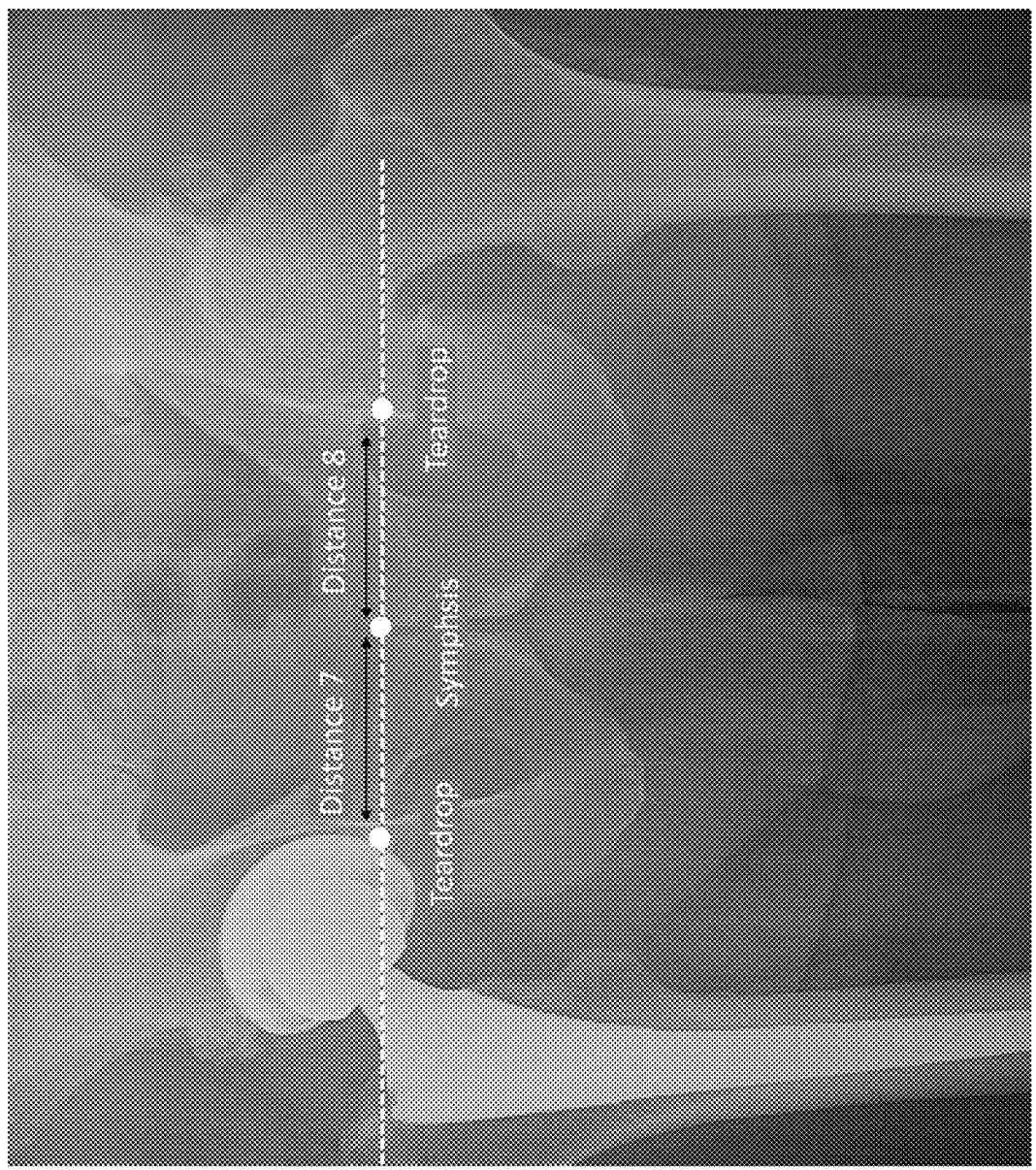

FIG. 4. is a diagrammatic representation of the three points on a lateral radiograph, such as shown and described in connection with FIG. 3. FIG. 4 illustrates how the measured distance between the three points, and the various distances previously obtained on an AP pelvis radiograph, can be used to calculate changes in sagittal pelvic tilt between two radiographs. For example, changes between calculated angles x, y, and z (FIG. 4) can be used to determine changes in sagittal pelvic position between AP radiographs.

In one or more implementations an artificial intelligence image recognition algorithm can be used to recognize certain anatomic landmarks to facilitate measurements of angles, distances or surface areas on a radiograph or fluoroscopic/C-Arm image (FIGS. 5A to 5E). Initially, one or more computing devices can be configured to identify anatomic landmarks that are usable to determine, among other distances, Distance 1 and Distance 2, Distance 3 and Distance 4, Distance 5 and Distance 6, Distance 7 and Distance 8. Moreover, the identified anatomic landmarks are usable to determine, among other angles and areas, Angle 1 and Angle 2, Area 1, Area 2 and Area 3. Such distances, angles, and areas can be based on, for example, pixel recognition within the image. Markers can be positioned substantially automatically within an image, according to such recognition.

Machine learning, including as further shown and described herein, can include corrections made by a human expert who can correct the position of one or more markers in order to increase the accuracy of one or more measurements and/or placements. Over time, machine learning provides for improvements and corrections, thereby increasing the accuracy of image recognition, measurements, and marker placements in connection with an image recognition algorithm. Accuracy improves until being within the range of a human expert. Accordingly, the present disclosure can provide for completely automatic and independent recognition of a patient's anatomic landmarks, which are usable to measure the variables shown and described herein.

In one or more implementations, artificial intelligence is used in connection with guided image recognition, including by using anatomic landmarks that are present in an image and automatically recognized. During machine learning, a pelvis AP radiograph is analyzed for locating a specific point, such as the pubic symphysis. A number of AP Pelvis images can be submitted for training, for example, by using tools provided by a GUI that are usable for marking the location of the symphysis using a rectangle with one of its corners being the location of the symphysis. For example, a rectangle is selected to define a set of unique (or close thereto) pixels to minimize a likelihood of error. Rectangles can be drawn on all the training AP Pelvis images and exported as a dataset. In one or more implementations, CREATE ML can be used for modeling, and a respective input file, such as compatible with CREATE ML, is generated and/or provided. CREATE ML provides a visual interface that is usable for training models using the CORE ML framework. Models are usable in connection with the present disclosure to accomplish a wide variety of tasks that would be otherwise difficult or impractical to write in programming code. Accordingly, a model trained to categorize images or perform other tasks, such as to detect specific anatomic landmarks (e.g., the symphysis) within an image (e.g., an AP Pelvis radiograph) as a function of pixels. Accordingly, in one or more implementations, an IOS application executes on a computing device IOS, e.g., an IPAD. Certain parameters are utilized in CREATE ML to optimize the training process for a particular case, including based on the number of images that are used, how recognizable the pixels are, the image colors, or other variables.

CORE ML is usable and optimized for hardware running IOS and provides a smooth and desirable user experience. Of course, one of ordinary skill will recognize that other modeling technologies and application development environments exist that are usable in connection with machine learning, artificial intelligence, and application (e.g., mobile app) development. Machine learning processes include executing an algorithm for a set of training images to create a model. Specific input is provided to identify a set of pixels (e.g., a rectangle selection) and to identify characteristics for training. The training can be an iterative process, in which the model tries to predict the location of the rectangle, including by comparing information that is determined from the selection with one or more values provided as an input. Furthermore, one or more entries can be used for teaching the model how to get closer to the desired output.

Following training, the model can be usable for automatic anatomical landmark detection and for predictive capabilities in connection with processing new input data. The model can analyze newly input AP pelvis images, for example, provided by the user, and the model reports a set of coordinates for the anatomic landmark (e.g., symphysis) based on what has been learned. Coordinates can be generated and, thereafter, used via a graphical user interface, for example, to draw a line or an ellipse based on what the software needs and to calculate angles and measure distances using basic equations, via one or more interfaces provided on a computing device, such as a mobile app running on a mobile device (e.g., an IPAD).

It is recognized herein that increasing axial rotation of the pelvis can result in changes in the appearance of a patient's Pelvis on an AP Pelvis OR fluoroscopy/C-Arm radiographs. The axial rotation of the pelvis, for example, results in an asymmetry of the left and right side of the pelvis. This can result in increasing differences between Distance 1 and Distance 2, Distance 3 and Distance 4, Distance 5 and Distance 6, and/or Distance 7 and Distance 8 (e.g., FIGS. 5A-5E). Further, this can result in increasing differences between Angle 1 and Angle 2, and/or Area 1 and Area 2. These differences can be correlated to the axial rotation calculated, such as shown and described herein.

As noted herein, the present disclosure provides for machine learning, which includes applying a plurality of images, depending on a respective implementation, training for an established, sound statistical or artificial intelligent correlation for variations represented over a plurality of images, as well as for measurements vis-à-vis a single image. The present disclosure includes one or more computing devices specially configured to recognize respective anatomical landmarks automatically and accurately, and to apply one or more respective calculations, such as shown and described herein, to predict an amount of axial rotation, sagittal drift, or other respective change or condition.

In one or more implementations of the present disclosure, differences between Distance 1 and Distance 2, Distance 3 and Distance 4, Distance 5 and Distance 6, and/or Distance 7 and Distance 8 (e.g., FIGS. 5A-5E) can be measured and used to predict and correct for axial rotation of the pelvis. Further such configured computing device(s) can predict and correct for an amount of rotation based on a difference between Angle 1 and Angle 2, and/or areas, such as Area 1 and Area 2 (e.g., FIGS. 5A-5E). The present disclosure provides for significantly improved accuracy, including as a function of calculated measurements on a lateral image of the pelvis (e.g., FIGS. 3A-3C and FIG. 4). Accordingly, the present disclosure can eliminate a need to determine axial rotation of an AP Pelvis Radiograph or C-arm/fluoroscopy image.

Further, changes in sagittal pelvic tilt between successive radiographs/Fluoroscopy/C-arm images can result in changes in Distance W, V and U (e.g., FIG. 1), Distance 1 and Distance 2, Distance 3 and Distance 4, Distance 5 and Distance 6 (e.g., FIGS. 5A-5E). Furthermore, changes result in Angle 1 and Angle 2, and Area 1 and Area 2 in relationship to Area 3 (e.g., FIGS. 5A-5E), between measurements from one image to the next image (e.g., in successive images). For example, such changes can be determined by identified in a preoperative AP radiograph and an intraoperative fluoroscopy/C-arm image) of the same patient. These differences can then be compared and correlated to calculate changes in Pelvic tilt and to adjust for implant placement.

Artificial intelligence provided as a function of machine learning and training using a sufficiently large number of images effectively establishes sound correlation between changes of the types shown and described herein. Moreover, using measurements for the same successive image, one or more computing devices configured in accordance with the teachings herein can predict changes in sagittal pelvic tilt from one image to the next (successive images of the same patient), including based on changes represented as a function of Distance W, V and U (e.g., FIG. 1), and Distance 1 and Distance 2, Distance 3 and Distance 4, Distance 5 and Distance 6 (e.g., FIGS. 5A-5E), as well as changes in Angle 1 and Angle 2, and Area 1 and Area 2 in relationship to Area 3 (e.g., FIGS. 5A-5E). Once provided with a high accuracy, the measurements on a lateral image of the pelvis (e.g., FIGS. 3A-3C and FIG. 4) can no longer be required to determine changes in sagittal pelvic tilt of successive AP Pelvis Radiographs AND/OR C-arm/fluoroscopy images of the same patient. Instead, changes in the variables, such as described herein, can be sufficient to predict the change in sagittal pelvic tilt.

Further, in one or more implementations the amount of axial rotation in degrees and the change in sagittal pelvic tilt in degrees can be correlated to changes in Distance 1, Distance 2, Distance 3, Distance 4, Distance 5, Distance 6, Distance 7, and/or Distance 8, and/or Angle 1, Angle 2 (FIGS. 5A-5E), and/or changes in surface areas including but not limited to Area 1, Area 2 and Area 3, as displayed in FIGS. 5A-5E. One or more specially configured computing devices can execute algorithms that include artificial intelligence and/or machine learning, to detect changes in distances, and 2-dimensional bone surface areas or the "appearance" of the AP pelvis image can be used to predict axial rotation or changes in sagittal pelvic tilt.

Thus, the methodology shown and described herein utilizes specific radiographic measurements on antero-posterior (AP) and lateral pelvis radiographs to determine changes in pelvic position in three dimensions. This is usable by surgeons to preoperatively plan or, alternatively (or in addition), intraoperatively assess changes in pelvic position and change in pelvic position between pelvic radiographs.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the points that follow, the respective features recited in those points, and by equivalents of such features.

Although many of the examples shown and described herein regard distribution of coordinated presentations to a plurality of users, the invention is not so limited. Although illustrated embodiments of the present invention have been shown and described, it should be understood that various changes, substitutions, and alterations can be made by one of ordinary skill in the art without departing from the scope of the present invention.

What is claimed is:

1. A computer-based system for image-guided implant placement, as a function of changes in patient position during a surgical procedure, the system comprising:
   at least one computing device configured by executing code stored in non-transitory processor readable media to:
   access an image captured at a first time and presenting a two-dimensional ("2-D") antero-posterior ("AP") view of a pelvis;
   automatically identify in the image captured at the first time and presenting the 2-D AP view of the pelvis, via a pixel-based artificial intelligence image recognition model, anatomical landmarks;
   automatically measure, using the identified anatomical landmarks in the image captured at the first time and presenting the 2-D AP view of the pelvis, first distances and angles;
   access an image captured at a second time and presenting a 2-D lateral view of the pelvis;
   automatically identify in the image captured at the second time and presenting the 2-D lateral view of the pelvis, via the pixel-based artificial intelligence image recognition model, the anatomical landmarks identified in the image captured at the first time and presenting the 2-D AP view of the pelvis;
   automatically measure, using the identified anatomical landmarks in the image captured at the second time and presenting the 2-D lateral view of the pelvis, second distances and angles;
   automatically determine, as a function of at least the measured first distances and angles and the measured second distances and angles, absolute axial rotation of the pelvis in the image captured at the first time and presenting the 2-D AP view of the pelvis;
   automatically determine, as a function of the measured second distances and angles, sagittal tilt of the pelvis in the image captured at the second time and presenting the 2-D lateral view of the pelvis;
   access during a surgical procedure, an image captured at a third time and presenting a 2-D AP view of the pelvis;
   automatically identify during the surgical procedure, in the image captured at the third time and presenting the 2-D AP view of the pelvis, via the pixel-based artificial intelligence image recognition model, the anatomical landmarks identified in the image captured at the first time and presenting the 2-D AP view of the pelvis;
   automatically measure during the surgical procedure, using the identified anatomical landmarks in the image captured at the third time and presenting the 2-D AP view of the pelvis, third distances and angles;
   automatically determine during the surgical procedure, at least as a function of the measured second distances and angles and the measured third distances and angles, absolute axial rotation of the pelvis in the image captured at the third time and presenting the 2-D AP view of the pelvis;

automatically determine during the surgical procedure, as a function of the measured first distances and angles, the measured second distances and angles, and the measured third distances and angles, a change in position of the pelvis in three-dimensional ("3-D") space, including a change in sagittal tilt of the pelvis, from the image captured at the first time and presenting the 2-D AP view of the pelvis to the image captured at the third time and presenting the 2-D AP view of the pelvis;

automatically determine during the surgical procedure, as a function of at least one of the determined absolute axial rotation of the pelvis in the image captured at the first time and presenting the 2-D AP view of the pelvis, the determined sagittal tilt of the pelvis in the image captured at the second time and presenting the 2-D lateral view of the pelvis, the second determined absolute axial rotation of the pelvis in the image captured at the third time and presenting the 2-D AP view of the pelvis, and the determined change in sagittal tilt of the pelvis, an adjustment to a position of an implant; and provide automatically determine during the surgical procedure, via a graphical user interface, information associated with the determined adjustment of the position of the implant.

2. The system of claim 1, wherein the at least one computing device is further configured by executing code to:
provide, via a graphical user interface:
a first line drawn between an inferior aspect of sacroiliac joints identified in at least one of the image captured at the first time and presenting the AP view of the pelvis and the image captured at the third time and presenting the AP view of the pelvis;
a second line drawn between an inferior aspect of acetabular teardrops identified in the at least one of the image captured at the first time and presenting the AP view of the pelvis and the image captured at the third time and presenting the AP view of the pelvis; and
a third line drawn between two most inferior ischia aspects identified in the at least one image captured at the first time and presenting the AP view of the pelvis and the image captured at the third time and presenting the AP view of the pelvis.

3. The system of claim 2, wherein the at least one computing device is further configured by executing code to:
measure at least one distance between a point on the first line, the second line and the third line.

4. The system of claim 1, wherein the at least one computing device is further configured by executing code to:
automatically determine, as a function of at least one navigational marker provided with the implant, the placement of the implant;
wherein adjusting the at least one value is based at least on the automatically determined position of the pelvis in 3-D space.

5. The system of claim 1, wherein the information associated with the at least one adjusted value includes at least one of positioning and repositioning the implant, and
further wherein the at least one computing device is further configured by executing code to automatically determine, as a function of at least one navigational marker provided with the implant, movement of the implant during the at least one of positioning and repositioning the implant.

6. The system of claim 1, wherein the at least one computing device is further configured by executing code to:
provide, via the graphical user interface, an alert associated with the placement of the implant.

7. The system of claim 6, wherein the alert is formatted at least as text, audio, video, an image, and embedded information.

8. The system of claim 1, wherein the at least one computing device is further configured by executing code to:
provide, via a graphical user interface:
a first point associated with a pubic symphysis anterior aspect on the image captured at the second time and presenting the lateral view of the pelvis;
a second point associated with an ischium inferior aspect on the image captured at the second time and presenting the lateral view of the pelvis; and
a third point associated with a sacrum meeting a posterior ilium on the image captured at the second time and presenting the lateral view of the pelvis.

9. The system of claim 8, wherein the at least one computing device is further configured by executing code to:
measure distances between the points,
wherein determining the value representing the change in sagittal pelvic tilt is further in accordance with the measured distances.

10. The system of claim 8, wherein the at least one computing device is further configured by executing code to:
measure distances between the points,
wherein determining at least one of the first value representing absolute axial rotation of the pelvis in the image captured at the first time and presenting the AP view of the pelvis, and the second value representing absolute axial rotation of the pelvis in the image captured at the third time and presenting the AP view of the pelvis, is further in accordance with the measured distances.

11. A computer-based method for image-guided implant placement, as a function of changes in patient position during a surgical procedure, the method comprising:
accessing, by at least one computing device configured by executing code stored in non-transitory processor readable media, an image captured at a first time and presenting a two-dimensional ("2-D") antero-posterior ("AP") view of a pelvis;
automatically identifying, by the at least one computing device, in the image captured at the first time and presenting the 2-D AP view of the pelvis, via a pixel-based artificial intelligence image recognition model, anatomical landmarks;
automatically measuring, by the at least one computing device, using the identified anatomical landmarks in the image captured at the first time and presenting the 2-D AP view of the pelvis, first distances and angles;
accessing, by the at least one computing device, an image captured at a second time and presenting a 2-D lateral view of the pelvis;
automatically identifying, by the at least one computing device, in the image captured at the second time and presenting the 2-D lateral view of the pelvis, via the pixel-based artificial intelligence image recognition model, the anatomical landmarks identified in the image captured at the first time and presenting the 2-D AP view of the pelvis;
automatically measuring, by the at least one computing device, using the identified anatomical landmarks in the image captured at the second time and presenting the 2-D lateral view of the pelvis, second distances and angles;

automatically determining, by the at least one computing device, at least as a function of the measured first distances and angles and the measured second distances and angles, absolute axial rotation of the pelvis in the image captured at the first time and presenting the 2-D AP view of the pelvis;

automatically determining, by the at least one computing device, as a function of the measured second distances and angles, sagittal tilt of the pelvis in the image captured at the second time and presenting the 2-D lateral view of the pelvis;

accessing during a surgical procedure, by the at least one computing device, an image captured at a third time and presenting a 2-D AP view of the pelvis;

automatically identifying during the surgical procedure, by the at least one computing device, in the image captured at the third time and presenting the 2-D AP view of the pelvis, via the pixel-based artificial intelligence image recognition model, the anatomical landmarks identified in the image captured at the first time and presenting the 2-D AP view of the pelvis;

automatically measuring during the surgical procedure, by the at least one computing device, using the identified anatomical landmarks in the image captured at the third time and presenting the 2-D AP view of the pelvis, third distances and angles;

automatically determining during the surgical procedure, by the at least one computing device, as a function of at least the measured second distances and angles and the measured third distances and angles, absolute axial rotation of the pelvis in the image captured at the third time and presenting the 2-D AP view of the pelvis;

automatically determining during the surgical procedure, by the at least one computing device, as a function of the measured first distances and angles, the measured second distances and angles, and the measured third distances and angles, a change in position of the pelvis in three-dimensional ("3-D") space, including a change in sagittal tilt of the pelvis, from the image captured at the first time and presenting the 2-D AP view of the pelvis to the image captured at the third time and presenting the 2-D AP view of the pelvis;

automatically determining during the surgical procedure, by the at least one computing device, as a function of at least one of the determined absolute axial rotation of the pelvis in the image captured at the first time and presenting the 2-D AP view of the pelvis, the determined sagittal tilt of the pelvis in the image captured at the second time and presenting the 2-D lateral view of the pelvis, the determined absolute axial rotation of the pelvis in the image captured at the third time and presenting the 2-D AP view of the pelvis, and the determined change in sagittal tilt of the pelvis, an adjustment to a position of an implant; and providing during the surgical procedure, by the at least one computing device, via a graphical user interface, information associated with the determined adjustment of the position of the implant.

12. The method of claim 11, further comprising:
providing, by at least one computing device via a graphical user interface:
 a first line drawn between an inferior aspect of sacroiliac joints identified in at least one of the image captured at the first time and presenting the AP view of the pelvis and the image captured at the third time and presenting the AP view of the pelvis;
 a second line drawn between an inferior aspect of acetabular teardrops identified in the at least one of the image captured at the first time and presenting the AP view of the pelvis and the image captured at the third time and presenting the AP view of the pelvis; and
 a third line drawn between two most inferior ischia aspects identified in the at least one image captured at the first time and presenting the AP view of the pelvis and the image captured at the third time and presenting the AP view of the pelvis.

13. The method of claim 12, further comprising:
measuring, by at least one computing device, at least one distance between a point on the first line, the second line and the third line.

14. The method of claim 11, further comprising:
automatically determining, by the at least one computing device as a function of at least one navigational marker provided with the implant, the placement of the implant;
wherein adjusting the at least one value is based at least on the automatically determined position of the pelvis in 3-D space.

15. The method of claim 11, wherein the information associated with the at least one adjusted value includes at least one of positioning and repositioning the implant, and further comprising automatically determining, by the at least one computing device as a function of at least one navigational marker provided with the implant, movement of the implant during the at least one of positioning and repositioning the implant.

16. The method of claim 11, further comprising:
providing, by the at least one computing device via the graphical user interface, an alert associated with the placement of the implant.

17. The method of claim 16, wherein the alert is formatted at least as text, audio, video, an image, and embedded information.

18. The method of claim 11, further comprising:
providing, by at least one computing device via a graphical user interface:
 a first point associated with a pubic symphysis anterior aspect on the image captured at the second time and presenting the lateral view of the pelvis;
 a second point associated with an ischium inferior aspect on the image captured at the second time and presenting the lateral view of the pelvis; and
 a third point associated with a sacrum meeting a posterior ilium on the image captured at the second time and presenting the lateral view of the pelvis.

19. The method of claim 18, further comprising:
measuring, by at least one computing device, distances between the points,
wherein determining the value representing the change in sagittal pelvic tilt is further in accordance with the measured distances.

20. The method of claim 18, further comprising:
measuring, by at least one computing device, distances between the points,
wherein determining at least one of the first value representing absolute axial rotation of the pelvis in the image captured at the first time and presenting the AP view of the pelvis, and the second value representing absolute axial rotation of the pelvis in the image captured at the third time and presenting the AP view of the pelvis, is further in accordance with the measured distances.

21. The method of claim 11, wherein the at least one value associated with placement of the implant includes determining, by the at least one computing device, at least one of inclination and anteversion.

22. The method of claim 21, wherein determining at least one inclination and anteversion is based on the change in axial rotation or absolute axial rotation of the pelvis and/or the change in sagittal tilt or determined sagittal tilt of the pelvis.

23. The method of claim 11, wherein the first time and the second time are before the third time.

\* \* \* \* \*

UNITED STATES PATENT AND TRADEMARK OFFICE
CERTIFICATE OF CORRECTION

| | |
|---|---|
| PATENT NO. | : 11,925,420 B2 |
| APPLICATION NO. | : 17/839203 |
| DATED | : March 12, 2024 |
| INVENTOR(S) | : Friedrich Boettner et al. |

It is certified that error appears in the above-identified patent and that said Letters Patent is hereby corrected as shown below:

On the Title Page

Item [71], should be changed to:
--ACCUPREDICT, INC.--

Signed and Sealed this
Thirtieth Day of April, 2024

Katherine Kelly Vidal
*Director of the United States Patent and Trademark Office*